(12) United States Patent
DeMarco et al.

(10) Patent No.: US 9,826,877 B2
(45) Date of Patent: *Nov. 28, 2017

(54) GEL WIPE COMPOSITION COMPRISING A SUPERABSORBENT GEL FIBER

(71) Applicant: Johnson & Johnson Consumer Inc., Skillman, NJ (US)

(72) Inventors: Gabriella Marie DeMarco, Basking Ridge, NJ (US); Euen Ekman-Gunn, Hopewell, NJ (US); John F. Poccia, III, Monmouth Beach, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/741,851

(22) Filed: Jun. 17, 2015

(65) Prior Publication Data

US 2016/0367102 A1 Dec. 22, 2016

(51) Int. Cl.

| D06M 15/09 | (2006.01) |
|---|---|
| B05D 1/18 | (2006.01) |
| A47L 13/17 | (2006.01) |
| A61K 8/02 | (2006.01) |
| A61K 8/72 | (2006.01) |
| A61K 8/81 | (2006.01) |
| A61Q 1/14 | (2006.01) |
| A61Q 19/00 | (2006.01) |
| A61Q 19/10 | (2006.01) |
| D04H 1/42 | (2012.01) |

(52) U.S. Cl.
CPC ............ *A47L 13/17* (2013.01); *A61K 8/0208* (2013.01); *A61K 8/72* (2013.01); *A61Q 1/14* (2013.01); *A61Q 19/10* (2013.01); *B05D 1/18* (2013.01); *D04H 1/42* (2013.01); *A61K 2800/54* (2013.01)

(58) Field of Classification Search
CPC ....... C11D 17/049; D06M 15/09; B05D 1/18; A47L 13/17; A61K 8/02; A61K 8/72; A61K 8/81; A61Q 1/14; A61Q 19/00
See application file for complete search history.

(56) References Cited

U.S. PATENT DOCUMENTS

| 4,366,206 A | 12/1982 | Tanaka |
|---|---|---|
| 4,374,175 A | 2/1983 | Tanaka |
| 4,507,204 A | 3/1985 | Tanaka et al. |
| 4,731,067 A | 3/1988 | Le-Khac |
| 4,743,244 A | 5/1988 | Le-Khac |
| 4,813,945 A | 3/1989 | Le-Khac |
| 4,873,143 A | 10/1989 | Tanaka |
| 4,880,868 A | 11/1989 | Le-Khac |
| 4,892,533 A | 1/1990 | Le-Khac |
| 5,026,784 A | 6/1991 | Le-Khac |
| 5,079,004 A | 1/1992 | Blank et al. |
| 5,079,080 A | 1/1992 | Schwarz |
| 5,079,306 A | 1/1992 | Le-Khac |
| 5,409,771 A | 4/1995 | Dahmen et al. |
| 5,466,731 A | 11/1995 | Akers et al. |
| 5,607,550 A | 3/1997 | Akers |
| 5,652,049 A | 7/1997 | Suzuki |
| 6,413,747 B1 | 7/2002 | Kato et al. |
| 6,992,054 B2 | 1/2006 | Lee et al. |
| 7,105,177 B1 | 9/2006 | Barney et al. |
| 7,718,249 B2 | 5/2010 | Russell et al. |
| 8,440,606 B2 | 5/2013 | Mundschau et al. |
| 8,906,839 B2 | 12/2014 | Lentsch et al. |
| 8,940,680 B2 | 1/2015 | Bernard et al. |
| 2004/0185730 A1 | 9/2004 | Lambino et al. |
| 2005/0159063 A1 | 7/2005 | Hill et al. |
| 2009/0018047 A1 | 1/2009 | Mundschau et al. |
| 2009/0081269 A1 | 3/2009 | Erazo-Majewicz et al. |
| 2010/0000116 A1 | 1/2010 | Aouad et al. |
| 2012/0121671 A1* | 5/2012 | Goldstein ............ D06M 15/03 424/401 |
| 2015/0174014 A1 | 6/2015 | Bruning et al. |

FOREIGN PATENT DOCUMENTS

JP  2000143484 A  5/2000

OTHER PUBLICATIONS

International Search Report dated Apr. 2, 2015 for PCT/US2014/069491.
International search report dated Jul. 22, 2016, for international application PCT/US2016/031406.

* cited by examiner

*Primary Examiner* — Brian P Mruk

(57) ABSTRACT

A fibrous gel-wipe, methods making the gel-wipe and methods of using the gel-wipe, suitable for use in personal care and household cleansing applications, which gel-wipe includes a superabsorbent gel fiber and a liquid cleansing composition.

20 Claims, No Drawings

GEL WIPE COMPOSITION COMPRISING A SUPERABSORBENT GEL FIBER

FIELD

The present invention relates to a fibrous gel-wipe suitable for use in personal care and household cleansing applications, which gel-wipe includes a superabsorbent gel fiber and a liquid cleansing composition.

BACKGROUND

Fibrous substrates, e.g. wipes, are known for use in personal care and household cleansing applications. Certain of the known wipes are dry, i.e., they do not include any liquid composition, cleansing or otherwise, impregnated onto or into the fibrous substrate. Other fibrous wipes do include liquid cleansing compositions impregnated onto the fibrous substrate and are referred to herein as wet wipes. Such cleansing compositions may include lathering surfactants and other ingredients for imparting cleansing or other desired properties to the wet wipe. One of the issues with such wet wipes is that the liquid composition may migrate from the fibrous substrate over time, resulting in decreased cleaning efficiency and waste of the cleansing composition.

To address the issue of migration of the liquid cleansing compositions from known wet wipes, certain gel-wipes for use in personal care and household cleansing applications have been disclosed. In some embodiments, such gel-wipes have a liquid portion that includes a thickening or gelling polymer and a thickening or gelling agent. The liquid portion containing the gelling polymer and the gelling agent is then impregnated in the fibrous substrate. In other embodiments, a gelling agent is incorporated into the substrate, followed by application of a liquid portion that contains the gelling polymer to the substrate having the impregnated gelling agent. In other embodiments, a fibrous substrate may be coated with a gelling material, exposing the gelling material to a neutralizing agent and then the gelling material is caused to swell, and finally, the liquid cleansing portion is applied to the wipe.

While such known gel-wipes are purported to reduce the migration of liquid from the wet-wipes, certain issues still exist with such gel-wipes. For example, the aforementioned wipes require multiple preparation steps to first apply the gelling material to the substrate and then apply the liquid cleaning material to the gelled wipe. That is, previous methods have incorporated a gelling polymer and/or neutralizing agent of the gelling polymer separate of a cleansing composition in order to create a gel layer in the wipe fibers. These prior methods add complexity to manufacturing, since they include more than one wipe coating step and use high viscosity solutions that may be difficult to process. In addition, the gel in such prior wipes has the potential to migrate off of the fabric, which can contaminate equipment and add challenges during manufacture.

It would be advantageous for one to develop a gel-wipe that not only provides as good as or better cleansing efficacy than gel-wipes described above, but that also allows for a more simplified preparation. The inventions set forth herein provide such gel-wipes that not only are at least as efficacious in cleansing compared to known gel-wipes, but also utilize fewer steps to prepare.

SUMMARY OF THE INVENTION

The subject matter of this application includes, among other aspects, gel-wipes, methods of making such gel-wipes, and methods of using such gel-wipes. The gel-wipes generally include a substrate including a plurality of first fibers and a plurality of second fibers, the first fibers including a superabsorbent polymer and the second fibers including a non-superabsorbent polymer, the substrate including a first surface, a second surface opposing the first surface, and a body disposed between and defined by the first and second surfaces; and a water-containing liquid cleansing composition applied to the substrate in an amount effective to provide swelling of the first fibers and to provide the liquid cleansing composition on at least one surface of the substrate.

There is also included a method of making a gel-wipe, the method including the steps of: providing a substrate including a plurality of first fibers and a plurality of second fibers, the first fibers including a superabsorbent polymer and the second fibers including a non-superabsorbent polymer, the substrate including a first surface, a second surface opposing the first surface, and a body disposed between and defined by the first and second surfaces; contacting the substrate with a water-containing liquid cleansing composition in an amount sufficient to cause swelling of the first fibers and allowing sufficient cleansing composition to remain on at least one surface of the substrate.

DETAILED DESCRIPTION

As used herein, the term "wet-wipe" refers to a fibrous substrate of woven, non-woven or knitted fabric which, during its manufacture, has a liquid cleansing composition, as defined herein, applied thereto, so that the liquid cleansing composition can be retained on or in the fibrous substrate where it is available for cleansing upon utilization by a consumer.

As used herein, the term "gel-wipe" refers to a fibrous substrate of woven, non-woven or knitted fabric which, during its manufacture, includes a gel material incorporated as part of the gel wipe, so that a liquid cleansing composition can be retained on or in the fibrous substrate where it is available for cleansing upon utilization by a consumer. The gel wipes of the present invention have a top surface and a bottom surface, with a middle portion therebetween. The gel wipes may be square, rectangular, oval, circular, or any other desired shape or configuration. Gel-wipes begin as dry wipes, and then are wetted as described above (to form a "wet-wipe").

As used herein, the term "superabsorbent gel fiber" refers to a fiber material that is made from a superabsorbent polymeric material. Superabsorbent polymeric materials include polymers capable of forming a polymeric gel when contacted with an appropriate gelling agent in amounts and under conditions effective to form the polymeric gel. The term "superabsorbent polymer" is understood to mean a polymer which is capable, in its dry state, of spontaneously absorbing at least about 10 times its own weight, or at least about 20 times its own weight of aqueous fluid, in particular of water and especially of distilled water. Such superabsorbent polymers are described in the work "Absorbent Polymer Technology, Studies in Polymer Science 8" by L. Brannon-Pappas and R. Harland, published by Elsevier, 1990, incorporated by reference herein in its entirety.

Superabsorbent polymers have a high capacity for absorbing and retaining water and aqueous fluids. After absorption of the aqueous liquid, the particles of the polymer thus impregnated with aqueous fluid remain insoluble in the aqueous fluid and thus retain their separated particulate state. The superabsorbent polymer can have a water-absorbing capacity ranging from 20 to 2000 times its own weight (i.e., 20 g to 2000 g of water absorbed per gram of absorbent polymer), preferably from 30 to 1500 times and better still ranging from 50 to 1000 times. These water-absorbing characteristics are defined at standard temperature (25° C.) and pressure (760 mm Hg, i.e. 100 000 Pa) conditions and for distilled water. The value of the water-absorbing capacity of a polymer can be determined by dispersing 0.5 g of polymer(s) in 150 g of a water solution, by waiting 20 minutes, by filtering the nonabsorbed solution through a 150 μm filter for 20 minutes and by weighing the nonabsorbed water.

Suitable examples of superabsorbent gel materials include, but are not limited to, cross-linked terpolymers based on acrylic acid, which is partially neutralized to its sodium salt, including those sold under the trade name Octacare X100, X110 and RM100 by Avecia, those sold under the names Flocare GB300 and Flosorb 500 by SNF, those sold under the names Luquasorb 1003, Luquasorb 1010, Luquasorb 1280 and Luquasorb 1100 by BASF, those sold under the names Water Lock G400 and G430 (INCI name: Acrylamide/Sodium Acrylate Copolymer) by Grain Processing, or Aqua Keep 10 SH NF, provided by Sumitomo Seika. starches grafted by an acrylic polymer (homopolymer or copolymer) and in particular by sodium polyacrylate, such as those sold under the names Sanfresh ST-100C, ST100MC and IM-300MC by Sanyo Chemical Industries (INCI name: Sodium Polyacrylate Starch), hydrolysed starches grafted by an acrylic polymer (homopolymer or copolymer), in particular the acryloacrylamide/sodium acrylate copolymer, such as those sold under the names Water Lock A-240, A-180, B-204, D-223, A-100, C-200 and D-223 by Grain Processing (INCI name: Starch/Acrylamide/Sodium Acrylate Copolymer), polymers based on starch, on gum and on cellulose derivative, such as those comprising starch, guar gum and sodium carboxymethyl cellulose, sold under the name Lysorb 220 by Lysac.

It is desirable to use fibers of a superabsorbent polymeric material, which has already included a neutralizing agent into the fiber itself. Therefore, the fibers to be used in preparing the substrate may be at least partially neutralized superabsorbent polymeric fibers. The fibers may be preformed or they may be cut to a desired size prior to use. The useful superabsorbent polymeric material is desirably substantially insoluble in water. A discussion of the manufacture of SAP fibers, for instance of polyacrylonitrile, can be seen in U.S. Pat. Nos. 4,873,143, 4,366,206, 4,374,175, and 4,507,204, the contents of each is incorporated by reference herein in their entireties. A discussion of the manufacture of SAP fibers, for instance of isobutylene/maleic anhydride copolymer, can be seen in U.S. Pat. Nos. 4,743,244, 4,813, 945, 4,880,868, 4,892,533, 4,731,067, 5,026,784, and 5,079, 306, the contents of each is incorporated by reference herein in their entireties. A discussion of the manufacture of SAP fibers, for instance of acrylic acid/methyl acrylate copolymers, can be seen In U.S. Pat. Nos. 6,413,747, 5,466,731, and 5,607,550, the contents of each is incorporated by reference herein in their entireties.

The SAP fibers may be manufactured on a large scale by continuous or discontinuous processes. More specifically, the SAP fiber of use in the present invention may include those manufactured by Technical Absorbents LTD UK under the tradename Oasis®/SAF™ or through Toyobo Japan Ltd under the tradename Lanseal®. It can also be manufactured by any known process for making SAP fibers. For instance, techniques may begin with an aqueous monomer solution, such as a solution of acrylic acid monomer, which is at least partially neutralized at some point. With solvent polymerization, the acid solution also contains a network cross-linking agent. Next, polymerization is initiated with radical initiators, such as thermal, redox, or photo initiators. After completion of polymerization, fibers are usually formed by extruding an aqueous solution of the polymer in its non-cross-linked state through a spinneret into a gaseous environment to remove the water to form a fiber or filament and subsequently cross-linking the polymer, preferably by heating.

The SAP fiber may be obtained by polymerizing at least about 10%, more preferably about 25%, and even more preferably about 55 to about 99.9% by weight of monomers having olefinically-unsaturated groups, such as acrylonitrile groups, anhydride groups, carboxylic acid groups, or sulfonic acid groups. Such carboxylic acid groups include, but are not limited to, acrylic acids, methacrylic acids, and maleic acids. An example of a sulfonic acid group is 2-acrylamido-2, methylpropane sulfonic acid. The groups are present as salts, such as sodium, potassium, or ammonium salts, i.e., the acrylate salt of acrylic acid.

The acid groups may be neutralized to at least about 25 mol %. Preferably, the extent of neutralization is to at least about 50 mol % up to about 80 mol %. More particularly, the preferred SAP fiber has been formed from cross-linked acrylic acid or methacrylic acid, which has been partially neutralized. Suitable neutralizing agents are hydroxides and/or carbonates of alkaline earth metals and/or alkali metals, for instance, of Na, K, Li, Be, Mg, Fe, Co, Ni, and the like.

Additional useful monomers for making the SAPs include ethers, imides, amides (such as acrylamide, methacrylamide, and dimethyl aminopropyl acrylamide), maleic acid, maleic anhydride, vinyl chloride, vinyl alcohol, styrene, acrylonitrile, isobutylene, isocyanate, esters (such as hydroxyethyl acrylate, hydroxypropyl acrylate, hydroxypropyl methacrylate, and dimethyl-aminoalkyl-methacrylate), and acrylamidopropyl trimethylammonium chloride.

Suitable network cross-linking agents useful in making the SAP fibers include those which can be activated (such as heat activated or photo-activated) after post-polymerization extrusion of the fiber or filament, for instance, those which have one ethylenically unsaturated double bond and one functional group reactive toward acid groups, and those which are multi-functional, i.e., have several functional groups reactive toward acid groups. Suitable network cross-linking agents include, but are not limited to, acrylate and methacrylate of polyols, such as hexapropylene glycol monomethacrylate. Suitable network cross-linking agents that are multi-functional include, but are not limited to, alcohols, amines, and epoxides, such as tris(hydroxymethyl) aminomethane, ethylene diamine, and diisocyanate. These network cross-linking agents are distinguished from and not to be confused with the surface cross-linking agents discussed below.

Furthermore, depending on the desired end use, the SAP fiber may have a water-soluble polymeric component. The content may range from above 0% to about 30% by weight of a component that includes, but is not limited to, partially or complete saponified polyvinyl alcohol, polyvinyl pyrrolidone, starch, starch derivatives, polyglycols, polyacrylic acids, and combinations thereof. The molecular weight of the component is not critical, provided that it is water-soluble. Preferred water-soluble polymeric components are starch, polyvinyl alcohol, and mixtures thereof. Preferably, the content of the water-soluble polymeric component in the SAP fiber ranges from about 1 to about 5% by weight, especially if starch and/or polyvinyl alcohol are present as the water-soluble polymeric component. The water-soluble polymeric component may be present as a graft polymer having the acid-groups-containing polymer.

SAP particles may be coated with an alkylene carbonate followed by heating to effect surface cross-linking More specifically, as described in U.S. Pat. No. 5,409,771, which is incorporated by reference herein in its entirety, to coat the SAP particles with a surface cross-linking agent (such as an alkylene carbonate, a polyol, a diamine, or a diepoxide), the SAP particles may be mixed with an aqueous-alcoholic solution of the surface cross-linking agent. The amount of alcohol is determined by the solubility of the alkylene carbonate and is kept as low as possible for technical reasons, for instance, protection against explosions. Suitable alcohols are methanol, ethanol, butanol, or butyl glycol, as well as mixtures of these alcohols. The preferred solvent is water which typically is used in an amount of 0.3 to 5.0% by weight, relative to the particulate SAP. In some instances, the alkylene carbonate surface cross-linking agent is dissolved in water, without any alcohol. It is also possible to apply the alkylene carbonate surface cross-linking agent from a powder mixture, for example, with an inorganic carrier material, such as $SiO_2$.

In the present invention, SAP fiber and surface cross-linking agent may be mixed by the SAP fiber being coated with the surface cross-linking agent, followed by heating to effect surface cross-linking Thus, the SAP fiber is surface cross-linked. It has been found with the present invention that (1) the surface X-linking agent may be mixed with the non-surface cross-linked SAP fiber and heat supplied to effect surface cross-linking absent the presence of any solvent and/or inorganic powder carrier; and (2) PEGs (such as PEG 200, PEG 300, PEG 600, or TPEG 990) are useful as a surface cross-linking agent, as are an alkylene carbonate, a diol, a diamine, or a diepoxide.

Compounds that have one or more groups capable of reacting with functional groups on the SAP may be employed as surface cross-linking agents, which includes all surface cross-linking agents disclosed in the aforementioned U.S. Pat. No. 5,409,771. Multivalent ions and their salts are also suitable, as well as structures with multiple charges on their surface.

For example, useful surface cross-linking agents include alkylene carbonates, which may include, e.g., 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxyethyl-1,3-dioxolan-2-one, 1,3-dioxan-2-one, 4-methyl-1,3-dioxan-2-one, 4,6-dimethyl-1,3-dioxan-2-one, 1,3-dioxepan-2-one, and combinations thereof. Preferred alkylene carbonates are 1,3,dioxolan-2-one and 4-methyl-1,3-dioxolan-2-one. A preferred diamine is 1,5-diaminopentane. Preferred diepoxides are 1,4-butanediol diglycidyl ether and 1,3-butadiene diepoxide. A preferred multivalent ion is trivalent aluminum.

As used herein, the term "polymeric gel" or "gel" refers to a gelled composition formed by combining a gelling polymer (described above) with a gelling agent, in amounts and under conditions effective to form the polymeric gel, for example, by reaction of the gelling polymer and agent, e.g. by crosslinking or neutralization, while the composition containing the gelling polymer is in contact with the substrate. In gel-wipes of the present invention, since the substrate includes a polymeric gel within the fibers themselves, which form the substrate body itself, the polymeric gel is distributed throughout the body of the substrate.

The gel wipes of the present invention include a fibrous substrate of woven, non-woven or knitted materials, where at least a portion of the fibers in the substrate are superabsorbent gel fibers. The gel wipe of the present invention should include a substantial amount of superabsorbent gel fibers as part of the substrate, including embodiments where at least about 15% of the fibers in the gel wipe are superabsorbent gel fibers, or at least about 20% of the fibers in the gel wipe are superabsorbent gel fibers, or at least about 25% of the fibers in the gel wipe are superabsorbent gel fibers (percentages are by weight of the dry substrate, prior to wetting). Less than 50% of the amount of fibers in the substrate should be superabsorbent fibers. The remaining fibers (referred to as "other fibers") in the gel wipe may be made from cellulosic pulp and/or man-made fibers. These other fibers may include, for example, natural and/or synthetic fibers, such as polypropylene, polyester, rayon, viscose, cotton, cellulose, cellulose derivatives, or mixtures thereof. More than one material may be included in the other fibers in the gel wipe. The superabsorbent gel fibers and the other fibers comprise 100% of the fibers in the substrate.

The gel wipe is formed by preparing the substrate from the superabsorbent gel fibers and other fibers to form the desired shape and configuration. The substrate may be woven or may be nonwoven, for example, it may be prepared by a spunlace process or other known processes to make a fiber-containing substrate. In addition to the fibers in the substrate, it will be understood that there will be interstitial spaces in the substrate body between the fibers. Typically, the substrate prior to wetting will have a thickness ranging from about 0.2 mm to about 2.0 mm, preferably from about 0.4 mm to about 1.0 mm, and most preferably about 0.4 mm to about 0.7 mm, as measured by ASTM D5729.

The gel wipes desirably have a desired level of resiliency, where the wipe may be compressed and have a desired level of "spring back". The level of resiliency may be determined by a separate test, using an AMES Thickness Testing Gage (Model BG1110-1-04 Resolution: 0.001" Circular Presser Foot: 1" diameter). In this method, a sample is first folded in half, and then the original thickness is determined with 0.5 oz weight. The presser foot is raised and a 0.5 oz weight is replaced with 1.0 oz weight, pressure reapplied and thickness measured. The presser foot is again raised, and the 1.0 oz weight is replaced with a 7.0 oz weight, pressure reapplied and thickness measured. Finally, the presser foot is raised, the 7.0 oz weight is removed and replaced with the original 0.5 oz weight, pressure reapplied and the "recovered" thickness is measured.

The gel wipes described herein may utilize thermal bonding to provide the required mechanical resistance between the fibers used to form the substrate. In some instances, the strength of the resulting wipe may be further enhanced by the addition of a binder, such as a latex emulsion or solution polymer, to provide a chemical bond between the fibers of the substrate.

The substrate is exposed to a liquid, such as a liquid cleansing composition, which is introduced to the gel wipe and allowed to penetrate into the interstitial spaces between the fibers. As the liquid penetrates the substrate, the aqueous portion of the liquid is seeped into the superabsorbent fibers, causing swelling of the superabsorbent fibers and reducing the interstitial spacing between fibers. Liquid may be contained within the substrate body and also on the top and/or bottom surfaces of the substrate. As used herein, the term "liquid cleansing composition" refers to a cleansing composition which provides the desired cleansing properties to the gel-wipe. The liquid cleansing composition may include, but is not limited to, water, emollients, detergents, surfactants, fragrances, preservatives, chelating agents, pH buffers, cleansing agents, or combinations thereof, as all are well known to those skilled in the art. The gel-wipe may contain the liquid cleansing composition in an amount of from about 2 to about 50%, or from about 4 to about 35%, and or about 4 to about 25% by weight of the wetted gel-wipe.

A liquid cleansing composition suitable for use in gel-wipes of the present invention may be a water-based formulation, in particular an aqueous solution. The composition may be emulsion-based, in which the emulsion can be water-in-oil or oil-in-water, or can be of more complex nature such as water-in-oil-in-water, or oil-in-water-in-oil or a self-organizing liquid crystalline emulsion. The composition also may include Pickering emulsions, micro-emulsions, oil-based solutions or formulations, and hydrodispersions. In one embodiment, the liquid cleansing composition is an oil-in-water emulsion. In another embodiment, the liquid cleaning composition is an oil-in-water emulsion prepared according to the phase inversion technique as known by those skilled in the art. In other embodiments the liquid cleansing composition may be a suspension or slurry that not only cleanses the body, but also soothes and heals the body, especially in babies and in the instance of compromised skin conditions.

Other ingredients that optionally can be included in the liquid cleansing compositions include, without limitation, stabilizers, water thickeners (such as cellulose ethers), oil phase thickeners and stabilizers, suspending agents, colorants, and other benefiting agents. Examples of benefiting agents include oil and fat and their derivatives, conditioning agents, soothing agents, healing agents, insect repellent agents, deodorizing agents, antibiotics, lubricants, luminance, vitamins, moisturizers, softening agents, antistatic agents, static agents, and mixtures thereof.

The liquid cleansing compositions of this invention may be formulated into a wide variety of personal care and household cleansing applications, including but not limited to liquid cleansers, creamy cleansers, gel cleansers, soaps, sanitizers and makeup removers. One particularly useful cleanser may include a cleanser that is mild and efficient enough to be used on young children, including babies, and may be capable of removing thick creams (such as diaper rash cream) from the skin of a baby.

The liquid cleansing compositions of the invention may contain a carrier, which should be a cosmetically and/or pharmaceutically acceptable carrier. The carrier should be suitable for topical application to the skin, should have good aesthetic properties and should be compatible with other components in the composition. These compositions may comprise several types of cosmetically acceptable topical carriers including, but not limited to, solutions, emulsions (e.g., microemulsions and nanoemulsions), gels, solids and liposomes.

As will be described in greater detail below, the present gel wipes are prepared by forming the substrate from the combination of superabsorbent gel fibers and non-absorbent (or less absorbent than superabsorbent fibers) gel fibers, and exposing the substrate to a liquid material, such as a cleansing liquid. Superabsorbent gel fibers, such as those provided by Technical Absorbents Grimsby UK, are blended with other fibers, such as those described above, to prepare a substrate. The fibers may, for example, be hydroentangled in a spunlace process or another process to create a nonwoven fabric, or the fabric may be woven by other methods. The resulting fabric substrate is then contacted with a water-containing liquid, which may be, for example, skincare cleansing liquids. The superabsorbent gel fibers are permitted to absorb water from the water-containing liquid to swell into a gel. The amount of water absorbed depends on the swelling potential of the superabsorbent fibers and the percentage of superabsorbent fibers incorporated into the wipe fabric. The swelling forms the resulting cleansing gel wipe. The wipe, when coated with liquids (including skincare cleansing liquids or solutions), exhibit an improved texture, with a full, cushiony and soft feel, as well as improved cleansing efficacy. The improvements are compared to a wipe that is free of superabsorbent gels or superabsorbent gel fibers.

In a previous method of forming a gel-containing wipe product, described in Applicant's co-pending U.S. application Ser. No. 14/134,123, filed Dec. 19, 2013, the entire disclosure of which is incorporated herein by reference, the wipe is made by a multi-step process. In this alternative method, a wipe substrate is first formed of fibers that are not superabsorbent gel-containing fibers. The substrate is coated with a gelling polymer, and then the coated substrate is gelled through exposure to a neutralizing agent. After the polymer is gelled, the wipe is then coated with the cleansing liquid. This method, along with other previous methods, utilizes separate steps of incorporating a gelling polymer and/or a neutralizing agent separate from the cleansing liquid. The gel is created through a series of steps, coating the wipe fibers with the gelling polymer, a neutralizer and a skincare lotion in a variety of different step sequences. In this prior invention, the gel forms both in the inner core of the fibers and in the pores between the fibers in the wipe fabric.

Although the previously described method is useful in preparing a suitable wipe that maintains its cleansing effectiveness, the aforementioned previous method utilizes several steps after formation of the fibrous substrate, whereas in contrast, the present invention seeks to provide a single-step swelling and loading process. That is, after formation of the substrate, the present invention uses one step to add liquid to the substrate, causing swelling and also loading the substrate with the liquid. The single-step preparation process described herein may provide a number of benefits, including ease of processing, reduced cost, and reduced likelihood of failure. Further, since the gel material is embedded into the substrate fibers (and not merely coated on the fibers, as in previous methods), there is reduced risk of loss of gel materials from the wipe. The gel is not permanently bound to the fibers or within the pores of the fabric, so has a potential to migrate out from the fabric.

The inventive sample utilizes a wipe fabric that has superabsorbent polymer cross-linked with the other wipe fibers, so the neutralized superabsorbent gelling polymers are permanently bound to the wipe fibers. This avoids the use of and need for a separate gel material to be applied to the surface of the fibers. The gel swells upon application of a water-containing material, such as a skincare cleansing solution as the superabsorbent polymers absorb water from the lotion. Unlike prior methods, the gel formation and skincare cleansing coating only require a single-step coating process, which simplifies and streamlines the wipe production process. The inventive substrate differs from previous substrates due to the capacity of inventive fibers to swell and expand within the structure of the substrate. The structure of the resulting gelled wipe therefore differs from previous examples. Since the superabsorbent polymers are present only within individual fibers, the gel forms only within the inner core of the fibers as the fibers swell upon absorption of water. Put another way, there is no gel material present in the pores between the fibers, and therefore only the skincare cleansing solution is present in the fabric pores.

The permanent binding of the superabsorbent polymers to the wipe fibers provides many benefits. The wipes better hold hydration, better retain the gel, prevent migration of skincare lotion and are more durable. Cleansing efficiency has improved in wipes made with the superabsorbent polymer fibers compared to wipes made with fibers without superabsorbent polymer. Since the neutralized superabsorbent gelling polymers are intrinsic in the wipe fibers, there exists a potential for reabsorption or reusable gelling capacity. The gel enhances wipe aesthetics by increasing wipe thickness, wipe hydration, cushioning effects and providing a smooth but firm feel of the gel The resulting gel wipes of the present invention have a desirable texture, with a full, cushiony and soft feel. As will be described in the Examples below, the present invention provides a gel wipe that has less resistance to pressure (a lower ratio of wipe thickness to applied load), giving it a soft feel, yet also has a "spring-back" characteristic. The amount of spring back may be measured by either the ASTM D5729 test described above or by using the AMES thickness testing gauge as also explained above. That is, the gel wipe may be compressed and the gel wipe will quickly return to its thickness prior to compression. The rate of spring back is quicker with the inventive gel wipe than with previous wipes tested.

The gel wipes described herein can substantially reduce friction and retain moisture, while providing a soft, soothing and gentle skin cleansing experience. Further, such gel-wipes minimize the amount of liquid cleansing solution, and thus cleansing surfactant, deposited on the gel-wipe substrate and therefore reduces irritation and improves its mildness, while achieving superior cleansing efficacy. In addition, such gel-wipes are more cost effective compared to known gel-wipes, which distribute the cleansing solution and gelling polymer throughout the substrate prior to introduction of the gelling agent to form a polymeric gel. As such, the major portion of cleansing solution trapped by and interspersed between the fibers is isolated from the surface to be cleaned and thus not able to contribute to cleansing, i.e., it is wasted. Gel-wipes of the present invention have utility as personal care wipes, such as baby wipes, cosmetic/facial wipes, wet toilet tissue, adult wipes, sanitizing wipes, intimate feminine care, personal cleansing, nail polish removers and hair remover pull strips.

The gel-wipes of the present invention, prior to gelling via addition of liquid cleansing composition, have a first shape and size, and then after gelling via addition of liquid cleansing composition have a second shape and size. The gel-wipe prior to addition of liquid is referred to as a dry gel-wipe (it is understood that there may be trace liquid, due to inherent moisture), and the gel-wipe prior to addition of liquid may be referred to as a wet gel-wipe. The substrate includes a combination of superabsorbent gel fibers and other fibers with interstitial spaces between the respective fibers used to form the substrate. The substrate has a top surface and bottom surface, with body therebetween, with the individual fibers randomly dispersed throughout the substrate. The substrate may contain from about 15% to about 50% superabsorbent gel fibers (by weight), or from about 20% to about 35% superabsorbent gel fibers (by weight), or from about 20% to about 30% superabsorbent gel fibers (by weight). The remaining fibers are other non-superabsorbent fibers, as described above. It is desired that the non-superabsorbent fibers be free of superabsorbent polymers. The substrate may be generally flat, with a top surface and a bottom surface and a middle region including the body therebetween. The surfaces may be irregular due to the irregular surfaces of the fibers comprising the substrate. It may have any shape or configuration desired, including, for example, rectangular, square, oval, circular or other configurations.

The thickness of the dry gel wipe prior to gelling is from about 0.50 to about 0.75 mm, or more particularly from about 0.60 to about 0.65 mm. If a rectangular wipe is used, the length may be from about 7 to about 10 inches, and more desirably about 7⅞ to about 8 inches; and the width may be about 5 to about 7 inches, and more desirably about 6 inches. If other shapes are used, such as circular, square, triangular, hexagonal, and the like, the cross sectional length, as defined by a line crossing the center of the wipe, may be about 5 to about 10 inches, or about 6 to about 7 inches.

The initial dry substrate is formed without the superabsorbent gel fibers having been subjected to a gelling process. A water-containing liquid is then introduced to the substrate, the water-containing liquid including sufficient water to cause gelling of at least a majority of the superabsorbent gel fibers in the substrate. The water containing liquid desirably includes at least one cleansing or other therapeutic agent, and specifically it desirably includes the cleanser to be used by a user of the product. The water containing liquid is permitted to contact the surfaces of the substrate and permeate through the interstitial spaces between the fibers. The final wetted product contains from about 2 to about 50% water containing liquid (by weight of the final product).

After the substrate has been subjected to the exposure to the water-containing liquid, the superabsorbent gel fibers begin to absorb water and swell due to gelling/crosslinking of the polymeric material within the gel fibers. Desirably, the superabsorbent gel fibers absorb as much water as they are capable of without added pressure or force, thereby swelling to an optimal degree. In some instances, the superabsorbent gel fibers free swell in 0.9% saline to a degree of 15 g/g to 100 g/g, more preferably 35 g/g to 60 g/g in 15 minutes, compared to swelling of a viscose fiber at 10 g/g. After swelling, there is no or only nominal increase in size of the non-superabsorbent fibers. Due to the swelling of the swelled superabsorbent gel fibers, the size of the interstitial spaces has decreased substantially, thereby restricting flow of liquid through and between adjacent fibers. The reduction in the interstitial spacing is important in that it serves to block or reduce the ability of liquid, including a cleansing liquid, to travel through the body of the gel wipe, and therefore it avoids problems where the cleanser travels through the wipes, settling into the bottom of the package into which the wipes are placed. This resulting configuration allows the cleanser to maintain in a coated state on each individual gel wipe, and therefore provides suitable and sufficient cleansing to the user. Of course, there is cleanser located within the body of the wetted gel-wipe as well. Due to physical attractive forces, not limited to intermolecular Van der Waals forces, the liquid cleansing compositions adhere to and coat the external surfaces of the substrate, including the surface of the swelled superabsorbent fibers. Thus, the liquid cleansing composition is maintained in proximity to the interstitial spaces within the substrate and the external cleaning surface of the gel-wipes. Therefore, the liquid cleansing composition is available for improved cleansing efficacy compared to gel-wipes of the prior art, where the liquid cleansing composition is incorporated into the gelling polymer solution prior to application to the substrate, and thus is bound or locked within the polymeric gel and unavailable for cleansing.

The above described process allows for the formation of a suitable gel wipe without having additional steps of immersing the substrate in a gel-containing material, coating the gel-containing material with a neutralizing agent to form a swelled gel, and then coating with a cleansing solution. Here, since the substrate is formed from a gel-containing fibrous material, the swelling and coating with cleansing solution can be achieved in one step.

A plurality of superabsorbent gel wipes (e.g., from about 10 to about 100, or from about 25 to about 50) may be prepared as described above by coating or otherwise subjecting the substrate with a water-containing cleansing solution, and packaged into a suitable package. The superabsorbent gel wipes may be stacked onto the surface of each other for ease of packaging and ultimate use by a consumer. In use, the user may open the package (which may be a resealable package), remove a cleansing solution-containing superabsorbent gel wipe, and cleanse a desired target with the superabsorbent wipe. In some embodiments, the desired target may be skin, such as facial skin or the skin of another individual, including a baby. After cleansing is complete, the user may wash off the target region, or the user may simply allow the cleansed target region to dry. The superabsorbent gel wipe may then be discarded. In some embodiments, the superabsorbent gel wipe may be reused, where the superabsorbent gel wipe is first coated with a cleansing material and then re-applied to a target region. The superabsorbent gel wipe may be reused, since the superabsorbent fibers within the gel wipe have already been gelled, and there is little to no loss of gel material from the gel wipe.

Examples

Four inventive sample wipes were prepared and three comparative sample wipes were prepared. Each wipe was prepared with one of three sample cleansing compositions, and each was tested for cleansing efficacy. Any water-containing cleansing compositions may be used in the present invention, and the below compositions are exemplary in nature and not intended to be limiting. One of the comparative wipes was prepared using a gel-containing method described in the Applicant's co-pending U.S. application Ser. No. 14/134,123.

Formation of Testing Surfaces

Vitro-Skin® with N-19 topography, an advanced testing surface that mimics the surface properties of human skin, and a plastic hydration chamber with mesh shelves (Complete VITRO-SKIN® N-19 Starter Kit) were obtained from IMS Inc., 110 Marginal Way, PMB, Portland Me., and was used to determine cleaning efficacy of comparative and inventive gel-wipes. First, a 2.5 gallon hydration chamber was prepared. The hydration chamber shelves were removed and all parts of the chamber were washed. 298 grams of purified water and 52 grams of glycerin were added to a clean beaker and were thoroughly mixed. Then, the glycerin-water solution was added to the bottom of the hydration chamber while being careful to not splash on shelves or walls of the chamber. The lid of the hydration chamber was kept on at all times except for when adding or removing the Vitro-Skin® substrate from the chamber.

One of three make-ups was applied to the Vitro-Skin® substrate prior to hydration. Specifically, one of Revlon® ColorStay Foundation in 450 Mocha for Oily Skin, Cover Girl® Lashblast Fusion Mascara 885 Very Black, or L'Oreal Paris® Infallible Eyeliner 511 Black was applied to the Vitro-Skin® substrate prior to hydration. Using a pencil, a circular test area of 2.54 cm (1") diameter was marked on the smooth side of the un-hydrated Vitro-Skin® substrate using a stencil. As many test areas as necessary were marked, leaving at least one centimeter between each test area. A positive displacement pipette was used to consistently expel and deposit 0.01 gram of foundation or mascara, or 0.006 g of eyeliner, to the middle of the marked circular test area on the rough side of the Vitro-Skin® substrate. The foundation was spread evenly around the circle, staying within the lines of the circle. The foundation was then left to air dry for about 20 minutes. This procedure was repeated for all test areas. After all test areas had air-dried, the Vitro-Skin® substrate containing the foundation was placed on the shelves in the hydration chamber. The lid of the hydration chamber was closed and the treated Vitro-Skin® substrate was allowed to hydrate for 12-24 hours.

Linear Makeup Removal Method

Each prepared wet wipe was wrapped around and secured to a 2 inch×4 inch sled (weighing 424 grams). The sled with the wet wipe was placed on a GARDCO Washability & Wear Tester—Linear Motion Test Equipment (Model# D10V, Catalog No WA-2153). A treated Vitro-Skin® substrate (2 inch×4 inch) was removed from the hydration chamber and affixed securely to the center of the base of the tester with masking tape. A 987 gram weight was placed on top of the sled containing the wet wipe. The test equipment was set to 3 cycles, the test speed was set at 5 inch/second and the unit engaged. The test material was applied to the Vitro-Skin® substrate with the foundation test circles. After the 3 cycles were completed, the Vitro-Skin® substrate was removed from the base and colorimeter measurements taken.

Colorimetry

After 30 minutes of drying, the color parameters of treated substrate samples were read on the Hunter LabScan XE Spectrophotometer (HunterLab, Reston, Va.). The Hunter LabScan XE Spectrophotometer was calibrated and standardized prior to reading each sample. Samples were placed on the Spectrophotometer with the makeup coated side up and the samples were read in the middle of the test circle. The white block was placed over the sample. Samples were read three times in the same spot and these readings were averaged so that each sample had one set of L*a*b values. After all samples had been read, a sample of stained Vitro-Skin (applied makeup without removal) and a sample of unstained Vitro-Skin (Vitro-Skin with no makeup applied) were read using the same process. After all samples had been read, the differences in color were calculated by taking the absolute value of the difference between the sample L, a, or b value and the stained standard L, a, or b value (dL, da, db). Next, the differences were combined to make a quantitative value between the two colors (dE). dE is represented by: $dE = \sqrt{dL^2 + da^2 + db^2}$. After dE is calculated for each sample, including the unstained sample, the percentage cleansing can be calculated by:

$$\% \text{ Cleansing} = \left(\frac{dE_{sample}}{dE_{unstained}}\right) \times 100$$

Baby Wipes Screening Test Method

The Baby Wipes Screening Test Method follows the same process as the Makeup Remover Screening Test Method with a few minor differences. For the Vitro-Skin® Testing Substrate Preparation, Desitin® Maximum Strength Original Paste is applied to the Vitro-Skin® substrate prior to hydration. For the Wet Wipes Preparation, the cleansing lotion was applied on top of the testing material with a pipette at a ratio of 3:1 (Lotion to Fabric). In the Linear Makeup Removal Process, no weight was placed on top of the sled containing the wet wipe. For the Colorimetry process, after the samples were placed on the spectrophotometer with the Desitin® coated side up so the sample could be read in the middle of the circle, the black block (to provide contrast to the white color of the Desitin®) was placed over the sample. Aside from these few differences, the rest of the process for the Baby Wipes Screening Test Method exactly followed the Makeup Remover Screening Test Method Process.

Wipe Compression and Recovery Measurement Test Method

AMES Thickness Testing Gage (Model BG1110-1-04, Resolution: 0.001", Circular Presser Foot: 1" diameter) was used to test the wipe thickness upon applied compression and recovery. Wipe samples were prepared using the Wet Wipes Preparation Process in the specified dimensions and lotion to fabric ratio. The wipe sample was folded in half and placed on the base of the AMES Gage under the raised presser foot. The original thickness was measured by applying 0.5 oz of presser foot weight, lowering the presser foot on the wipe and measuring the thickness in millimeters. After the original thickness is determined, the presser foot was raised from the sample and the 0.5 oz weight was replaced with a 1.0 oz weight, the pressure foot was applied and the compressed thickness was measured. This process was repeated with a 7.0 oz weight. The recovery of the wipe thickness was measured by raising the pressure foot and replacing the 7.0 oz weight with the original 0.5 oz weight, applying the pressure foot and measuring the thickness.

Liquid Cleansing Compositions

A liquid cleansing composition (J1) was prepared. Premix 1: The organic diol and branched ester A (0.75 w/w %) were mixed in a beaker. Then the fatty acid triglyceride, branched ester B (2.00 w/w %), and suitable preservative A (0.40 w/w %) and B (0.30 w/w %) were added to the mixer with continuous mixing for 30-35 minutes. Premix 2: In a separate beaker, branched ester C (2.00 w/w %), branched ester D (2.50 w/w %) and DUB PTO (14150) were mixed until homogenous. Then the Silicone-based cyclic compound (volatile silicone) and preservative C (0.09 w/w %) were added and mixed until homogenous. Main Phase: In a third beaker, purified water and the acrylate crosspolymer were mixed until dissolved. Premix 1 was combined with the Main Phase and mixed for 20-30 minutes. Then, Premix 2 was added to the mixture and mixed for another 20-30 minutes. Initial pH was measured and the basic solution was added to the mixture to adjust the pH to between 5.0 and 6.0.

TABLE 1

| J1 Liquid Cleansing Composition | | |
|---|---|---|
| Component | Function | w/w % |
| Organic Diol(s) | Surfactant, emulsifying agent | 1.00 |
| Branched Esters | Emollient, Surfactant, Moisturizing agent | 7.25 |
| Fatty Acid Triglycerides | Skin conditioning agent, emollient | 0.75 |
| DUB PTO (14150) | Emollient | 2.50 |
| Silicone based cyclic compound (volatile silicone) | Conditioning agent, emollient, solvent | 2.00 |
| Preservatives | Preservative | 0.79 |
| Purified Water | Solvent | 85.32 |

TABLE 1-continued

| J1 Liquid Cleansing Composition | | |
|---|---|---|
| Component | Function | w/w % |
| Acrylate Crosspolymer | Thickening agent | 0.21 |
| Basic Solution | pH Adjustment | 0.18 |
| | TOTAL | 100.00 |

A second liquid cleansing composition (J2) was prepared. Premix 1: Add the organic diol to the beaker and begin mixing and heating to 65-70° C. While heating and mixing at medium speed, add suitable preservative A (0.27 w/w %) to the beaker. Mix the premix for 5-10 minutes or until clear and uniform. Oil Phase Preparation: In a second beaker, add branched ester A (2.00 w/w %) and mix at a low-medium speed. While mixing, add branched ester B (2.00 w/w %) and suitable preservative B (2.00) and mix for 2-5 minutes or until homogenous. Maintain mixing until ready for phasing. Main Phase: In a third beaker, add purified water. Using a Lab Homogenizer, add the acrylate crosspolymer and homogenize for 10-20 minutes or until uniformly dispersed. Then, mix at medium speed and add the glycerin, suitable preservative C (0.50 w/w %), Premix 1, branched ester C (0.10 w/w %) and branched ester D (0.75 w/w %). Increase the mixing speed to medium-high and mix the batch to 30-60 minutes or until homogenous. Phasing: Add the Oil Phase to the Main Phase and mix for 10-20 minutes or until homogenous. Post Phase: Record initial pH and add the appropriate amount of basic solution to get the target pH of 5.4. Mix for 5-10 minutes and record the final pH and final viscosity.

TABLE 2

| J2 Liquid Cleansing Composition | | |
|---|---|---|
| Component Classification | Function | w/w % |
| Organic Diol(s) | Surfactant, emulsifying agent | 1.00 |
| Branched Esters | Emollient, Surfactant, Moisturizing agent | 4.85 |
| Preservatives | Preservative | 2.77 |
| Purified Water | Solvent | 89.74 |
| Acrylate Crosspolymer | Thickening agent | 0.14 |
| Glycerin | Smoothness, lubrication, humectancy | 1.00 |
| Basic Solution | pH Adjustment | 0.50 |
| | TOTAL | 100.00 |

A second liquid cleansing composition (J2) was prepared. Premix 1: The organic diol and branched ester A (0.75 w/w %) were mixed in a beaker. Then the fatty acid triglyceride, branched ester B (2.00 w/w %), and suitable preservative A (0.40 w/w %) and B (0.30 w/w %) were added to the mixer with continuous mixing for 40-45 minutes. Premix 2: In a separate beaker, branched ester C (2.00 w/w %), branched ester D (2.50 w/w %), DUB PTO (14150), the alcohol alkoxylate and Dibetaine UB 3544 were mixed for 30-35 minutes. Then, the Silicone-based cyclic compound (volatile silicone) was added and mixed for 12-15 minutes. Then, preservative C (0.09 w/w %) was added and mixed for 20 minutes. Main Phase: Add purified water to the main beaker. Add Premix 1 and mix for 12-15 minutes. Then, add Premix 2 and mix for 12-15 minutes.

TABLE 3

J3 Liquid Cleansing Composition

| Component Classification | Function | w/w % |
| --- | --- | --- |
| Organic Diol(s) | Surfactant, emulsifying agent | 1.00 |
| Branched Esters | Emollient, Surfactant, Moisturizing agent | 7.25 |
| Fatty Acid Triglycerides | Skin conditioning agent, emollient | 0.75 |
| DUB PTO (14150) | Emollient | 2.50 |
| Alcohol alkoxylate | Surfactant | 2.00 |
| Dibetaine UB 3544 | Surfactant | 2.00 |
| Silicone based cyclic compound (volatile silicone) | Conditioning agent, emollient, solvent | 2.00 |
| Preservatives | Preservative | 0.79 |
| Purified Water | Solvent | 81.67 |
| TOTAL | | 99.96 |

Dry Wipe Samples

Three comparative dry wipe samples (C1, C2, C3) were prepared and four inventive dry wipe samples (E1, E2, E3, E4) were prepared. The dry wipe samples were prepared with the specifications of Table 4.

TABLE 4

Dry Wipes

| Wipe ID | Fiber Blend | Target Basis Weight (gsm) | Target Thickness Actual Thickness (mm) (Test Method ASTM D5729) | Pattern |
| --- | --- | --- | --- | --- |
| C1 | Blend of 20% Lenzing Viscose Fiber (1.7 dtex, 40 mm)/80% Trevira Trilobel Polyester (1.7 dtex, 38 mm) | 60 | 0.58 | Plain |
| C2 | Blend of 20% Lenzing Viscose, (1.7 dtex, 40 mm)/80% Far Eastern W3 Polyester (1.7 dtex, 38 mm) | 60 | 0.56 | Plain |
| C3 | Blend of 20% Lenzing Viscose (1.7 dtex, 40 mm)/40% Polyester (1.3 dtex, 38 mm)/40% Polyester Trilobal (1.7 dtex, 38 mm) | 50 | 0.43 | Plain |
| E1 | Blend of 20% Technical Absorbents SAF Type 112/52/10 (9 dtex, 50 mm)/80% Far Eastern W3 Polyester (1.7 dtex, 38 mm) | 60 | 0.63 | Plain |
| E2 | Blend of 20% Technical Absorbents SAF Type 112/52/10 (9 dtex, 50 mm)/20% Lenzing Viscose (1.7 dtex, 40 mm)/60% Far Eastern W3 Polyester (1.7 dtex, 38 mm) | 60 | 0.63 | Plain |
| E3 | Blend of 20% Technical Absorbents SAF Type 122/52/10 (9 dtex/50 mm)/80% Far Eastern W3 Polyester (1.7 dtex, 38 mm) | 60 | 0.60 | Plain |
| E4 | Blend of 20% Technical Absorbents SAF Type 122/52/10 (9 dtex/50 mm)/80% Far Eastern W3 Polyester (1.7 dtex, 38 mm) | 60 | 0.61 | Plain |

Preparation of Wet Wipe Samples

Ten wet wipe samples were made with various combinations of the dry wipe samples and the liquid compositions described above.

Comparative Sample 1 was prepared by using the C1 dry wipe and J1 liquid cleansing composition. A dry testing fabric material was cut to 6 inch×7⅞ inch, folded in quarters and weighed. The cleansing lotion was applied on top of the testing material with a pipette at a ratio of 3.7:1 (Lotion to Fabric by weight). The Sample was pressed gently to make sure the entire solution was absorbed and spread evenly around the material.

Comparative Sample 2 was prepared by using the C2 dry wipe and J1 liquid cleansing composition. A dry testing fabric material was cut to 6 inch×7⅞ inch, folded in quarters and weighed. The cleansing lotion was applied on top of the testing material with a pipette at a ratio of 3.7:1 (Lotion to Fabric by weight). The Sample was pressed gently to make sure the entire solution was absorbed and spread evenly around the material.

Comparative Sample 3 was prepared by using the C3 dry wipe and J2 liquid cleansing composition. A dry testing fabric material was cut to 6 inch×7⅞ inch, folded in quarters and weighed. The cleansing lotion was applied on top of the testing material with a pipette at a ratio of 7.4:1 (Lotion to Fabric by weight). The testing material was pressed gently to make sure the entire solution was absorbed and spread evenly around the material.

Comparative Sample 4 was prepared by using the C3 dry wipe and J3 liquid cleansing composition. First, the dry wipe was immersed into 25 grams of 0.25% Carbomer solution. Once the wipe was completely submerged, the wipe was left in solution for one minute to saturate the substrate with Carbomer solution. After the submersion, the wipe was removed from the Carbomer solution, folded into fourths (longitudinally) and the excess Carbomer was removed from the wipe. The wipe was drained from top to bottom using two gloved fingers, squeezing gently so as to remove the excess Carbomer solution and then the wipe was flipped over and once again drained from top to bottom with two fingers. After the wipe was drained from the 0.25% Carbomer solution, the wipe was immersed in 25.0 grams of a 1% NaOH solution for one minute, after which time it was removed from the solution and excess solution was removed using the same drainage process as described above. The resulting gel-wipe substrate comprised a polymeric gel distributed throughout the substrate and inner core of a portion of the fibers. Upon completion of the formulation of the substrate comprising the polymeric gel, the wipe was immersed for one minute in the J3 Liquid Cleansing Composition, after which time it was removed from the solution and excess solution removed via the drainage process described above. It is noted that Comparative Sample 4 is that described and claimed in Applicant's Co-Pending application Ser. No. 14/134,123.

Inventive Sample 1 was prepared by using the E1 dry wipe and J1 liquid cleansing composition. A dry testing fabric material was cut to 6 inch×7⅞ inch, folded in quarters and weighed. The cleansing lotion was applied on top of the testing material with a pipette at a ratio of 3.7:1 (Lotion to Fabric by weight). The Sample was pressed gently to make sure the entire solution was absorbed and spread evenly around the material.

Inventive Sample 2 was prepared by using the E2 dry wipe and J1 liquid cleansing composition. A dry testing fabric material was cut to 6 inch×7⅞ inch, folded in quarters and weighed. The cleansing lotion was applied on top of the testing material with a pipette at a ratio of 3.7:1 (Lotion to Fabric by weight). The Sample was pressed gently to make sure the entire solution was absorbed and spread evenly around the material.

Inventive Sample 3 was prepared by using the E3 dry wipe and J1 liquid cleansing composition. A dry testing fabric material was cut to 6 inch×7⅞ inch, folded in quarters and weighed. The cleansing lotion was applied on top of the testing material with a pipette at a ratio of 3.7:1 (Lotion to Fabric by weight). The Sample was pressed gently to make sure the entire solution was absorbed and spread evenly around the material.

Inventive Sample 4 was prepared by using the E4 dry wipe and J1 liquid cleansing composition. A dry testing fabric material was cut to 6 inch×7⅞ inch, folded in quarters and weighed. The cleansing lotion was applied on top of the testing material with a pipette at a ratio of 3.7:1 (Lotion to Fabric by weight). The Sample was pressed gently to make sure the entire solution was absorbed and spread evenly around the material.

Inventive Sample 5 was prepared by using the E4 dry wipe and J2 liquid cleansing composition. A dry testing fabric material was cut to 6 inch×7⅞ inch, folded in quarters and weighed. The cleansing lotion was applied on top of the testing material with a pipette at a ratio of 7.4:1 (Lotion to Fabric by weight). The testing material was pressed gently to make sure the entire solution was absorbed and spread evenly around the material.

Inventive Sample 6 was prepared by using the E4 dry wipe and J3 liquid cleansing composition. First, the dry wipe was immersed into 25 grams of Carbomer solution. Once the wipe was completely submerged, the wipe was left in solution for one minute to saturate the substrate with Carbomer solution. After the submersion, the wipe was removed from the Carbomer solution, folded into fourths (longitudinally) and the excess Carbomer was removed from the wipe. The wipe was drained from top to bottom using two gloved fingers, squeezing gently so as to remove the excess Carbomer solution and then the wipe was flipped over and once again drained from top to bottom with two fingers. After the wipe was drained from the 0.25% Carbomer solution, the wipe was immersed in 25.0 grams of a 1% NaOH solution for one minute, after which time it was removed from the solution and excess solution was removed using the same drainage process as described above. The resulting gel-wipe substrate comprised a polymeric gel distributed throughout the substrate and inner core of a portion of the fibers. Upon completion of the formulation of the substrate comprising the polymeric gel, the wipe was immersed for one minute in the J3 Liquid Cleansing Composition, after which time it was removed from the solution and excess solution removed via the drainage process described above.

Makeup Removal and Baby Wipe Screening Method Using J1 Cleansing Composition

Comparative 1 and Comparative 2, as well as Inventive 1, Inventive 2, Inventive 3, and Inventive 4 were evaluated and compared for cleansing efficacy using the Makeup Removal Screening Test Method and the Baby Wipes Screening Test Method described above. The results for the makeup removal screening method are presented in Table 5 below:

TABLE 5

| Wipe Example | Comparative 1 | Comparative 2 | Inventive 1 | Inventive 2 | Inventive 3 | Inventive 4 |
| --- | --- | --- | --- | --- | --- | --- |
| Average % Cleansing | 12 | 9 | 20 | 23 | 17 | 13 |
| Standard Deviation | 6.3 | 3.7 | 7.8 | 8.1 | 6.9 | 5.2 |

For the makeup removal screening test method, inventive examples Inventive 1, Inventive 2 and Inventive 3 have significantly higher cleansing efficacy than comparative example 2 (p values <0.05). Only inventive example Inventive 2 has significantly higher cleansing efficacy than comparative example 1 (p=0.024). Inventive example Inventive 4 did not have a significantly different cleansing efficacy than either of the comparative examples, which demonstrates at least a comparable cleansing effect when compared to the comparative examples.

The results for the Baby Wipes Screening Test Method are presented in Table 6 below:

TABLE 6

| Wipe Example | Comparative 1 | Comparative 2 | Inventive 1 | Inventive 2 | Inventive 3 | Inventive 4 |
| --- | --- | --- | --- | --- | --- | --- |
| Average % Cleansing | 20 | 16 | 40 | 40 | 44 | 44 |
| Standard Deviation | 2.5 | 2.8 | 2.1 | 4.5 | 4 | 3.2 |

The results clearly demonstrate that the cleansing efficacies of the inventive samples are comparable to the efficacies of the comparative examples in the Makeup Remover Screening Test Method. The inventive samples exhibit significant improvement in cleansing efficacy when compared to the comparative wipes in the Baby Wipes Screening Test Method. This is evidenced by the fact that all inventive examples have significantly higher cleansing efficacy compared to both comparative examples (p values <0.00001).

Makeup Removal Using J2 and J3 Cleansing Compositions

Comparative 3 and Comparative 4, as well as Inventive 5 Inventive 6 were evaluated and compared for cleansing efficacy using the Makeup Removal Screening Test Method described above. The results are presented in Table 7 below:

TABLE 7

| Wipe Example | Revlon ® ColorStay 450 Mocha | | Cover Girl ® Lashblast Fusion Mascara 885 Very Black | | L'Oréal Paris ® Infallible Eyeliner 511 Black | |
|---|---|---|---|---|---|---|
| | Average % Cleansing | Standard Deviation | Average % Cleansing | Standard Deviation | Average % Cleansing | Standard Deviation |
| Comparative 3 | 15.5 | 3.7 | 19.9 | 7.9 | 14.7 | 5.5 |
| Inventive 5 | 18.7 | 4.7 | 16.3 | 3.2 | 20.0 | 2.6 |
| Comparative 4 | 18.3 | 5.2 | 44.0 | 8.3 | 16.1 | 4.3 |
| Inventive 6 | 11.5 | 2.6 | 39.0 | 8.1 | 19.3 | 3.4 |

Comparative 3 and Inventive 5 were prepared by the same process as each other, and with the same cleansing composition. Comparative 4 and Inventive 6 were prepared by the same process as each other, and with the same cleansing composition. The results demonstrate that the inventive samples demonstrate comparable cleansing efficacies to the comparative samples for various types of makeup.

Compression Recovery

Comparative 3, Comparative 4, as well as Inventive 5 and Inventive 6 were evaluated and compared for compression and recovery thickness using the Wipe Compression and Recovery Measurements process described above. Results for the Wipe Compression and Recovery Measurements are presented in Table 8 below:

TABLE 8

| Applied | Wipe Example: | | | |
|---|---|---|---|---|
| Load (oz): | Comparative 3 | Inventive 5 | Comparative 4 | Inventive 6 |
| | Average Thickness in mm (Standard Deviation): | | | |
| 0.5 | 0.94 (0.04) | 1.37 (0.08) | 0.91 (0.03) | 1.28 (0.11) |
| 1.0 | 0.89 (0.04) | 1.30 (0.07) | 0.86 (0.04) | 1.21 (0.13) |
| 7.0 | 0.76 (0.03) | 1.04 (0.03) | 0.74 (0.02) | 1.00 (0.05) |
| 0.5 | 0.84 (0.06) | 1.26 (0.03) | 0.84 (0.04) | 1.23 (0.06) |
| Percentage Recovery (%) | 89.36 | 91.97 | 92.31 | 96.09 |

The results clearly display the increased wipe thickness in the inventive samples when compared to the comparative samples. As noted above, Comparative 3 and Inventive 5 were prepared by the same process as each other, and with the same cleansing composition. Comparative 4 and Inventive 6 were prepared by the same process as each other, and with the same cleansing composition. The inventive wipes when compared to the similar counterpart demonstrate an increased initial thickness and a larger percentage recovery of the thickness than the comparative wipes.

We claim:

1. A gel-wipe comprising:
    a substrate comprising a plurality of first fibers and a plurality of second fibers, said first fibers consisting essentially of a superabsorbent polymer and said second fibers comprising a non-superabsorbent polymer, said substrate comprising a first surface, a second surface opposing said first surface, and a body disposed between and defined by said first and second surfaces; and
    a water-containing liquid cleansing composition applied to said substrate in an amount effective to provide swelling of said first fibers and to provide said liquid cleansing composition on at least one surface of the substrate.

2. The gel-wipe of claim 1, wherein said first fibers consist of a superabsorbent polymer.

3. The gel-wipe of claim 2, wherein said first fibers are present in an amount of about 20% by weight of said gel-wipe.

4. The gel-wipe of claim 1, wherein said first fibers comprise a superabsorbent polymer and a neutralizing agent.

5. The gel-wipe of claim 1, wherein said second fibers are free of a superabsorbent polymer.

6. The gel-wipe of claim 1, wherein said swelling increases the volume of said gel-wipe by about 20% to about 150% as compared to the gel-wipe prior to addition of said water-containing liquid cleansing composition.

7. The gel-wipe of claim 1, wherein said gel-wipe is free of gelling material outside of said first fibers.

8. The gel-wipe of claim 1, wherein said substrate is selected from the group consisting of woven, non-woven and knitted fabrics.

9. The gel-wipe of claim 2, wherein said superabsorbent polymer is selected from the group consisting of cross-linked terpolymers based on acrylic acid, sodium alginate, carboxymethylcellulose, guar gum and derivatives thereof, hydroxyethyl guar, carboxymethyl guar, methylguar, hydroxypropylmethyl guar, cationic guar, cationic hydrophobically modified guar, anionic hydrophobically modified guar, hydrophobically modified guar and borax; pectin gum, carrageenan gum; polyvinyl alcohol, cross linked polyacrylic acid, xanthan gum, gellan gum and ionic polymer or surfactant having a charge.

10. The gel-wipe of claim 9, wherein said second fibers are comprised of materials consisting of polyester, polypropylene, rayon, cotton, and combinations thereof.

11. The gel-wipe of claim 1, comprising from about 2 percent to about 50 percent of said liquid cleansing composition by weight of said gel-wipe.

12. A method of making a gel-wipe, the method comprising the steps of:
    providing a substrate comprising a plurality of first fibers and a plurality of second fibers, said first fibers consisting essentially of a superabsorbent polymer and said second fibers comprising a non-superabsorbent polymer, said substrate comprising a first surface, a second surface opposing said first surface, and a body disposed between and defined by said first and second surfaces;
    contacting said substrate with a water-containing liquid cleansing composition in an amount sufficient to cause swelling of said first fibers and allowing sufficient cleansing composition to remain on at least one surface of said substrate.

13. The method of claim 12, wherein said first fibers consist of a superabsorbent polymer.

14. The method of claim 12, wherein said first fibers are present in an amount of about 20% by weight of said gel-wipe.

15. The method of claim 12, wherein said first fibers comprise a superabsorbent polymer and a neutralizing agent.

16. The method of claim 12, wherein said second fibers are free of a superabsorbent polymer.

17. The method of claim 12, wherein said swelling increases the volume of said gel-wipe by about 20% to about 150% as compared to the gel-wipe prior to addition of said water-containing liquid cleansing composition.

18. The method of claim 12, wherein said gel-wipe is free of gelling material outside of said first fibers.

19. The method of claim 12, wherein said superabsorbent polymer is selected from the group consisting of cross-linked terpolymers based on acrylic acid, sodium alginate, carboxymethylcellulose, guar gum and derivatives thereof, hydroxyethyl guar, carboxymethyl guar, methylguar, hydroxypropylmethyl guar, cationic guar, cationic hydrophobically modified guar, anionic hydrophobically modified guar, hydrophobically modified guar and borax; pectin gum, carrageenan gum; polyvinyl alcohol, cross linked polyacrylic acid, xanthan gum, gellan gum and ionic polymer or surfactant having a charge.

20. The method of claim 12, comprising from about 2 percent to about 50 percent of said liquid cleansing composition by weight of said gel-wipe.

* * * * *